(12) United States Patent
Barshinger et al.

(10) Patent No.: US 7,234,354 B2
(45) Date of Patent: Jun. 26, 2007

(54) ULTRASONIC PROBE AND INSPECTION METHOD AND SYSTEM

(75) Inventors: James Norman Barshinger, Scotia, NY (US); Richard Eugene Klaassen, West Chester, OH (US)

(73) Assignee: General Electric Company, Niskayuna, NY (US)

( * ) Notice: Subject to any disclaimer, the term of this patent is extended or adjusted under 35 U.S.C. 154(b) by 242 days.

(21) Appl. No.: 11/004,567

(22) Filed: Dec. 3, 2004

(65) Prior Publication Data

US 2006/0117855 A1 Jun. 8, 2006

(51) Int. Cl.
G01N 29/26 (2006.01)
G01N 29/265 (2006.01)
G01N 29/04 (2006.01)
(52) U.S. Cl. .............. 73/619; 73/642; 73/644
(58) Field of Classification Search .......... 73/644
See application file for complete search history.

(56) References Cited

U.S. PATENT DOCUMENTS

| 3,918,297 | A | * | 11/1975 | Rocha | 73/607 |
|---|---|---|---|---|---|
| 4,055,990 | A | * | 11/1977 | Topping | 73/623 |
| 4,149,419 | A | * | 4/1979 | Connell et al. | 73/621 |
| 4,297,886 | A | * | 11/1981 | Anikeev et al. | 73/642 |
| 4,554,834 | A | * | 11/1985 | Prinz et al. | 73/597 |
| 4,580,451 | A | * | 4/1986 | Miwa et al. | 73/626 |
| 5,787,049 | A | * | 7/1998 | Bates | 367/7 |
| 6,591,680 | B2 | | 7/2003 | Batzinger et al. | |
| 6,654,502 | B1 | * | 11/2003 | Aldrich et al. | 382/236 |
| 6,789,427 | B2 | | 9/2004 | Batzinger et al. | |
| 6,792,808 | B1 | | 9/2004 | Batzinger et al. | |

OTHER PUBLICATIONS

Josef Krautkramer and Herbert Krautkramer, "Ultrasonic Testing of Materials", 1977, Springer-Verlag Berlin Heidelberg New York, p. 620.*
N. Barshinger et al., "Two Dimensional Phased Arrays for Voumetric Ultrasonic Inspection and Methods of Use," U.S. Appl. No. 10/686,756, filed Oct. 16, 2003.

* cited by examiner

Primary Examiner—Hezron Williams
Assistant Examiner—Rose M. Miller
(74) Attorney, Agent, or Firm—Penny A. Clarke; Patrick K. Patnode

(57) ABSTRACT

A method of inspecting a component includes immersing the component in a coupling medium with material velocity $c_w$ and immersing an ultrasonic (UT) probe having at least one transducer in the coupling medium. The UT probe has a convex lens with acoustic velocity $c_L$ and an acoustic impedance less than about $2.5 \times 10^6$ Rayls. The method further includes exciting the transducer to produce an UT pulse directed into the component and generating echo signals using the transducer as a receive element. An US inspection system includes UT probe, a pulser/receiver configured to supply signal excitation pulses to the transducer element at a pulse repetition frequency (prf) of at least about 1000 Hz and a scanner configured to scan the component with the UT probe at a scanning rate equal to the prf times a scanning increment.

13 Claims, 8 Drawing Sheets

ULTRASONIC PROBE AND INSPECTION METHOD AND SYSTEM

BACKGROUND

The invention relates generally to ultrasonic immersion testing of industrial components and, more particularly, to reducing unattenuated sound in a coupling medium to increase testing speed in an ultrasonic immersion inspection.

Ultrasonic testing is a desirable inspection technique for industrial components. However, conventional ultrasonic immersion inspection techniques have limited throughput as a result of the unattenuated sound that reverberates in the coupling medium that is being used to couple ultrasonic energy to the component under test. FIG. 1 depicts a conventional A-scan (amplitude vs. time) display for an ultrasonic immersion test. As indicated in FIG. 1, a number of echoes occur beyond the testing region, which are caused by unattenuated sound. Consequently, conventional immersion ultrasonic scans require relatively long intervals between ultrasonic pulses, in order to permit the echos to decay before the subsequent ultrasonic pulse. FIG. 2 shows a conventional A-scan display for an ultrasonic immersion test where the second ultrasonic pulse occurs before the echo from the first ultrasonic pulse has decayed to an acceptable level. As indicated in FIG. 2, the echo impairs the accuracy with which a flaw can be detected. Because there is generally no method to distinguish between an echo caused by a defect within the test object or an echo caused by unattenuated sound, the presence of an echo caused by unattenuated sound will be interpreted as a defect, resulting in a false positive. The phenomenon of echoes associated with unattenuated sound is generally termed "wraparound" or "ghosting." To reduce the noise associated with the unattenuated sound, conventional ultrasonic immersion tests are run at relatively low pulse repletion frequencies (prf), for example at five hundred pulses per second (500 pulses/s). Due to the low prfs that must be employed, inspection of a typical aircraft engine component may take on the order of four hours using conventional techniques.

It would therefore be desirable to reduce the unattenuated sound for ultrasonic immersion testing. It would further be desirable to reduce the time necessary to inspect industrial components using ultrasonic immersion inspection techniques.

BRIEF DESCRIPTION

An aspect of the present invention resides in a method of inspecting a component that includes immersing the component in a coupling medium with a material velocity $c_w$ and immersing an ultrasonic probe with at least one transducer in the coupling medium. The ultrasonic probe further includes a convex lens with an acoustic velocity $c_L$ and an acoustic impedance of less than about $2.5 \times 10^6$ Rayls. The method further includes exciting the transducer to produce an ultrasonic pulse directed into the component and generating a number of echo signals using the transducer as a receive element.

Another aspect of the invention resides in an ultrasonic inspection system for testing a component using a coupling medium. The ultrasonic inspection system includes an ultrasonic probe having (a) at least one transducer element configured to produce an ultrasonic pulse directed into the component through the coupling medium upon excitation and to generate a number of echo signals, and (b) a convex lens having an acoustic impedance of less than about $2.5 \times 10^6$ Rayls. The convex lens is ultrasonically coupled to each of the transducer elements. The ultrasonic inspection system further includes a pulser/receiver configured to supply a number of signal excitation pulses to the transducer element at a pulse repetition frequency (prf) of at least about 1000 Hz and a scanner configured to scan the component with the ultrasonic probe at a scanning rate equal to the prf times a scanning increment.

Another aspect of the invention resides in an ultrasonic probe for immersion inspection of industrial components in a coupling medium with a material velocity $c_w$. The ultrasonic probe includes at least one transducer element configured to produce an ultrasonic pulse directed into the industrial component through the coupling medium upon excitation and to generate a number of echo signals. The ultrasonic probe further includes a convex lens having an acoustic impedance of less than about $2.5 \times 10^6$ Rayls and a F# of at least about four (4). The convex lens is ultrasonically coupled to each of the transducer elements.

DRAWINGS

These and other features, aspects, and advantages of the present invention will become better understood when the following detailed description is read with reference to the accompanying drawings in which like characters represent like parts throughout the drawings, wherein.

Figure 7:
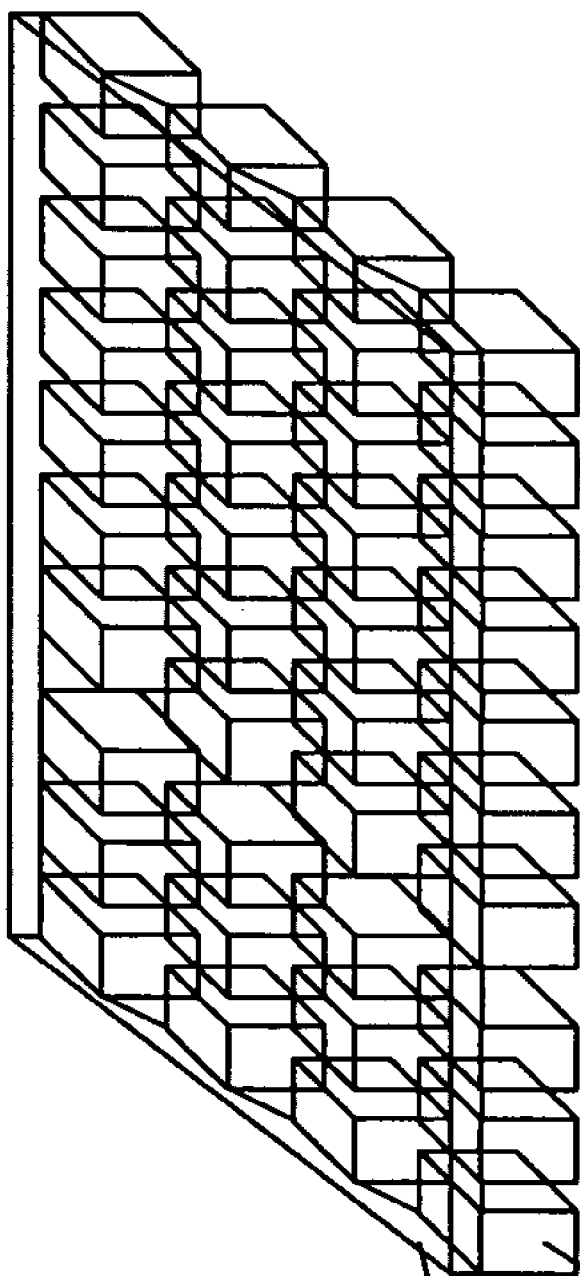
Figure 8:
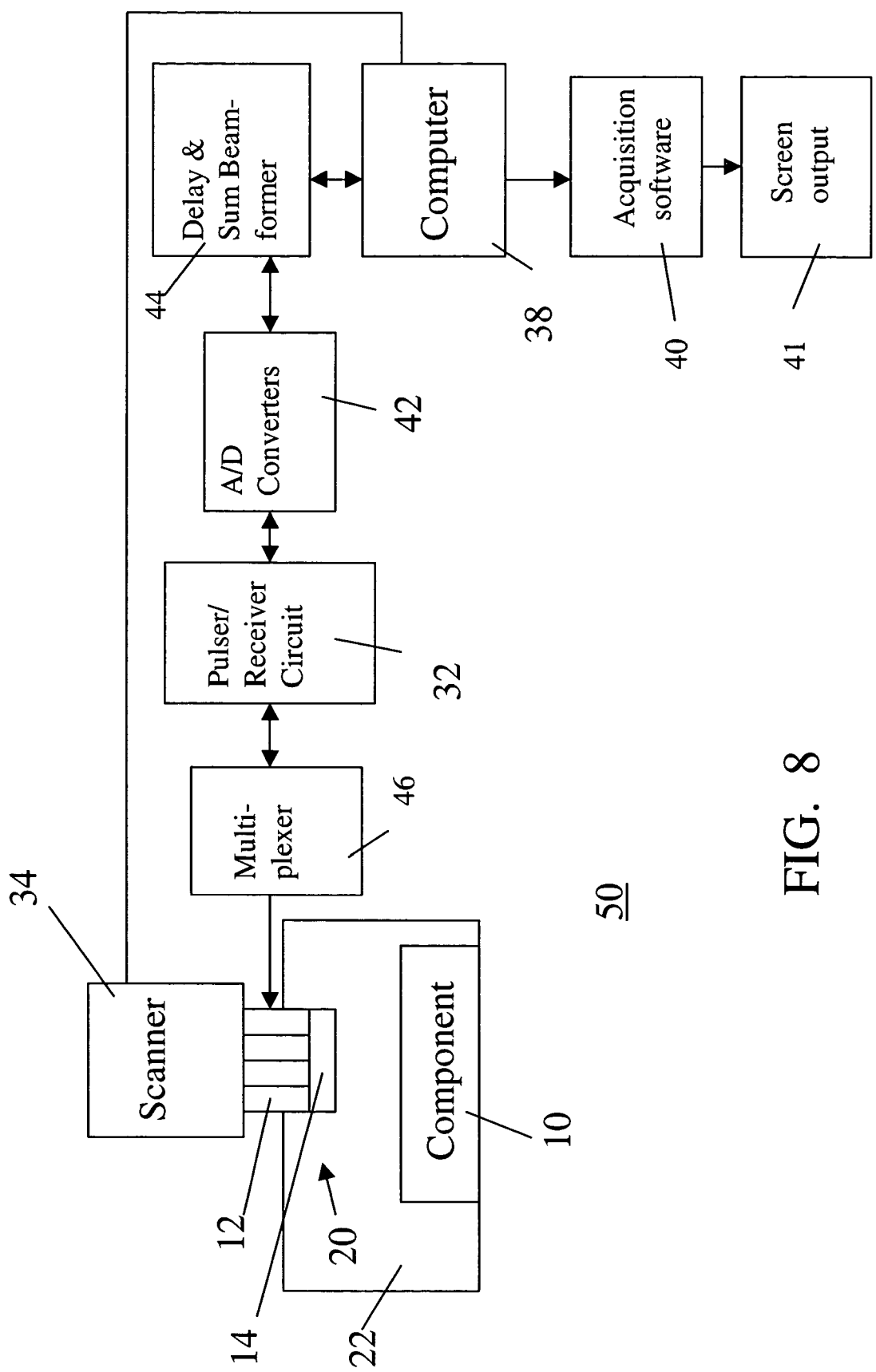

FIG. 7 schematically depicts a two-dimensional phased array of ultrasonic transducers with a single convex lens; and FIG. 8 depicts another ultrasonic inspection system embodiment of the invention.

DETAILED DESCRIPTION

An ultrasonic inspection system 30 embodiment of the invention is described with reference to FIG. 3. As indicated, ultrasonic inspection system 30 is configured for testing a component 10, such as an industrial component 10, using a coupling medium 22. An exemplary coupling medium 22 is water, and exemplary industrial components 10 include aircraft engine components, such as fan disks. As shown, ultrasonic inspection system 30 includes an ultrasonic probe 20 that includes at least one transducer element 12 configured to produce an ultrasonic pulse directed into the component 10 through the coupling medium 22 upon excitation and to generate a number of echo signals. Ultrasonic probe 20 also includes at least one convex lens 14 having an acoustic impedance of less than about $2.5 \times 10^6$ Rayls. One Rayl is equal to one Newton-second per cubic meter (Ns/$m^3$). Convex lens 14 is ultrasonically coupled to each transducer element. As used herein, the phrase "convex lens" includes a plano-convex lens.

Figure 1:
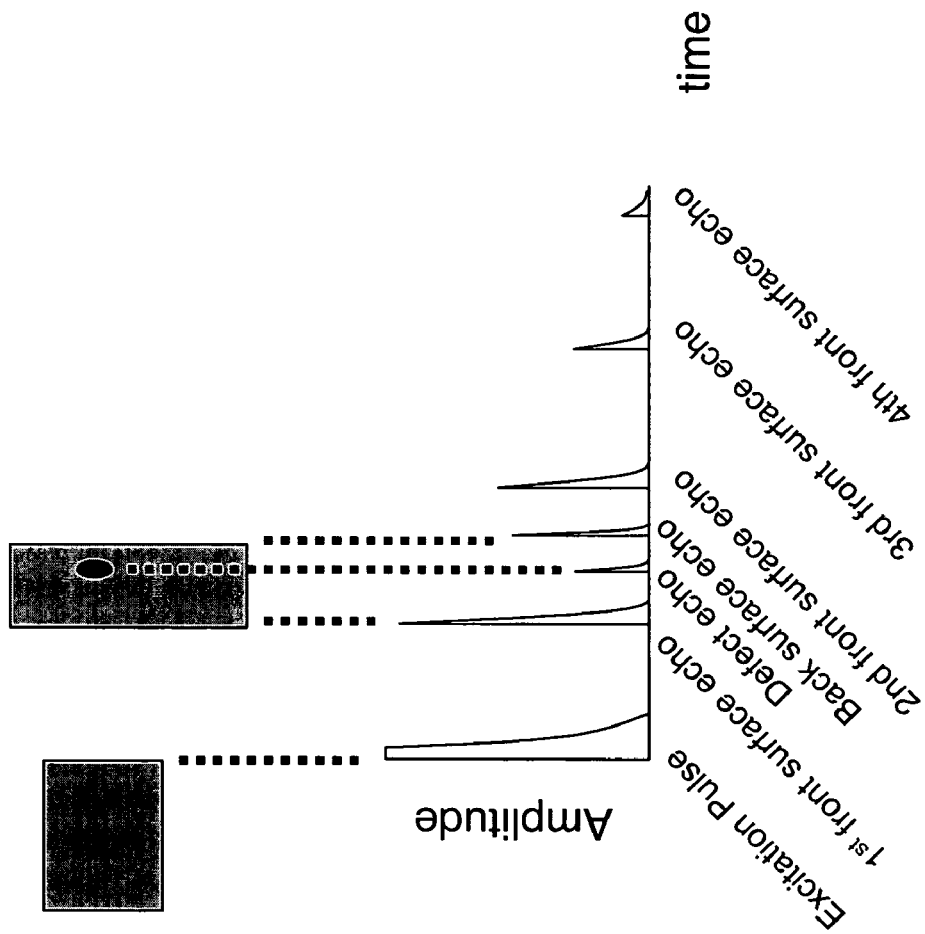
FIG. 1 depicts a conventional A-scan (amplitude vs. time) display for an ultrasonic immersion test.
Figure 2:
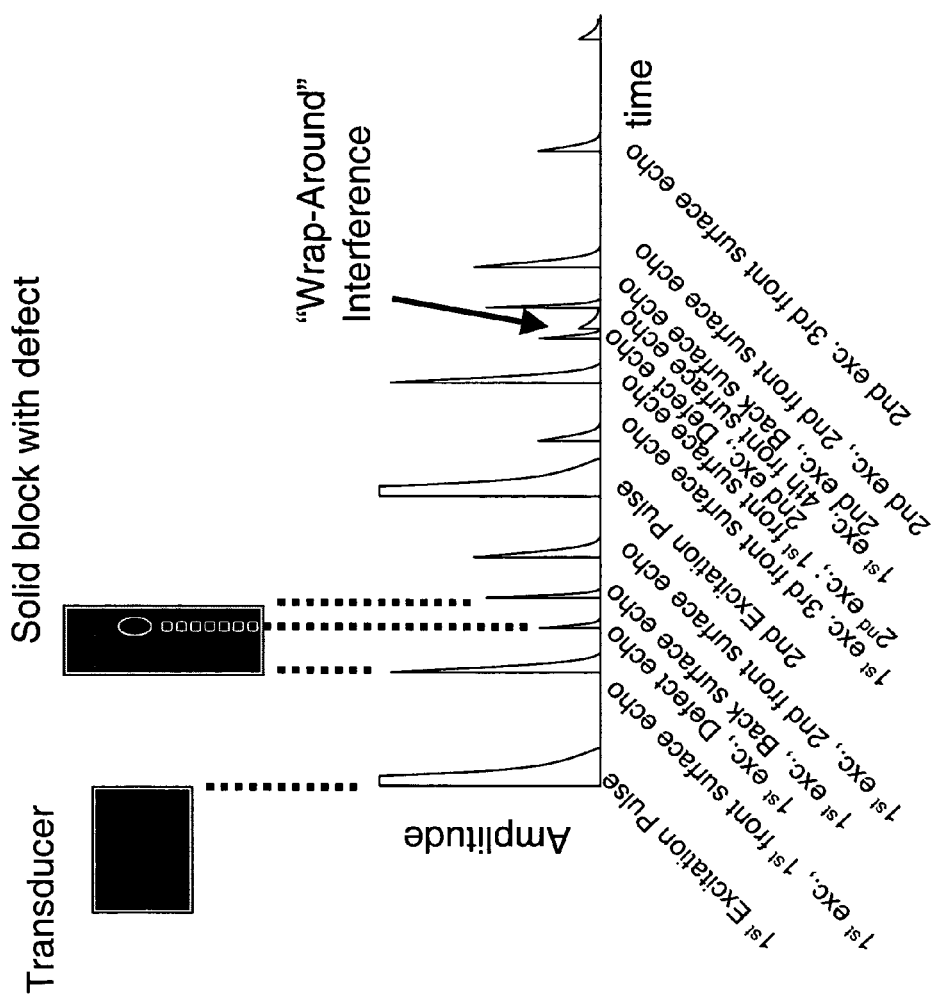
FIG. 2 shows a conventional A-scan display for an ultrasonic immersion test where the second ultrasonic pulse occurs before the echo from the first ultrasonic pulse has decayed to an acceptable level.
Figure 3:
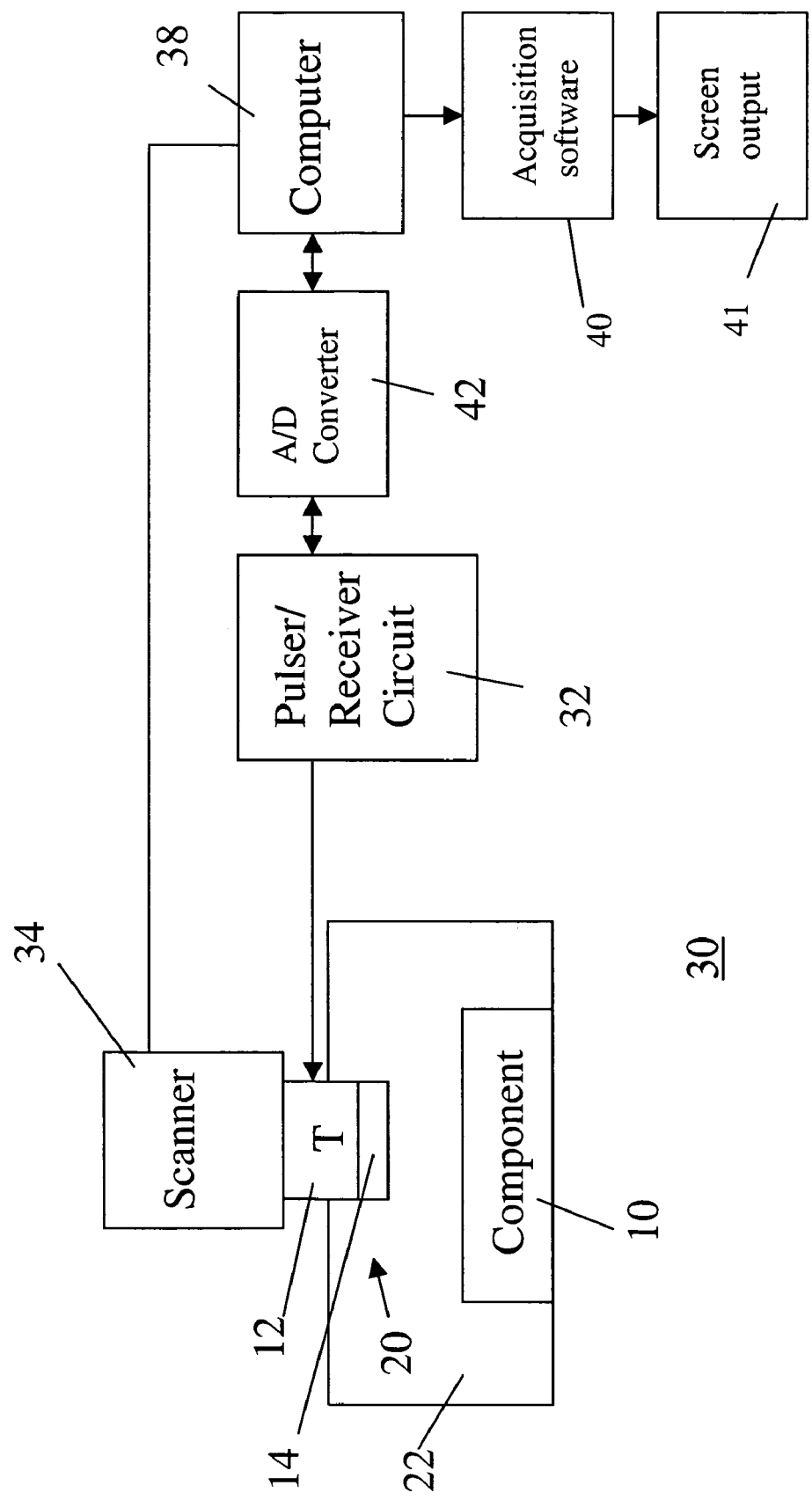
FIG. 3 depicts an ultrasonic inspection system embodiment of the invention.
Figure 6:
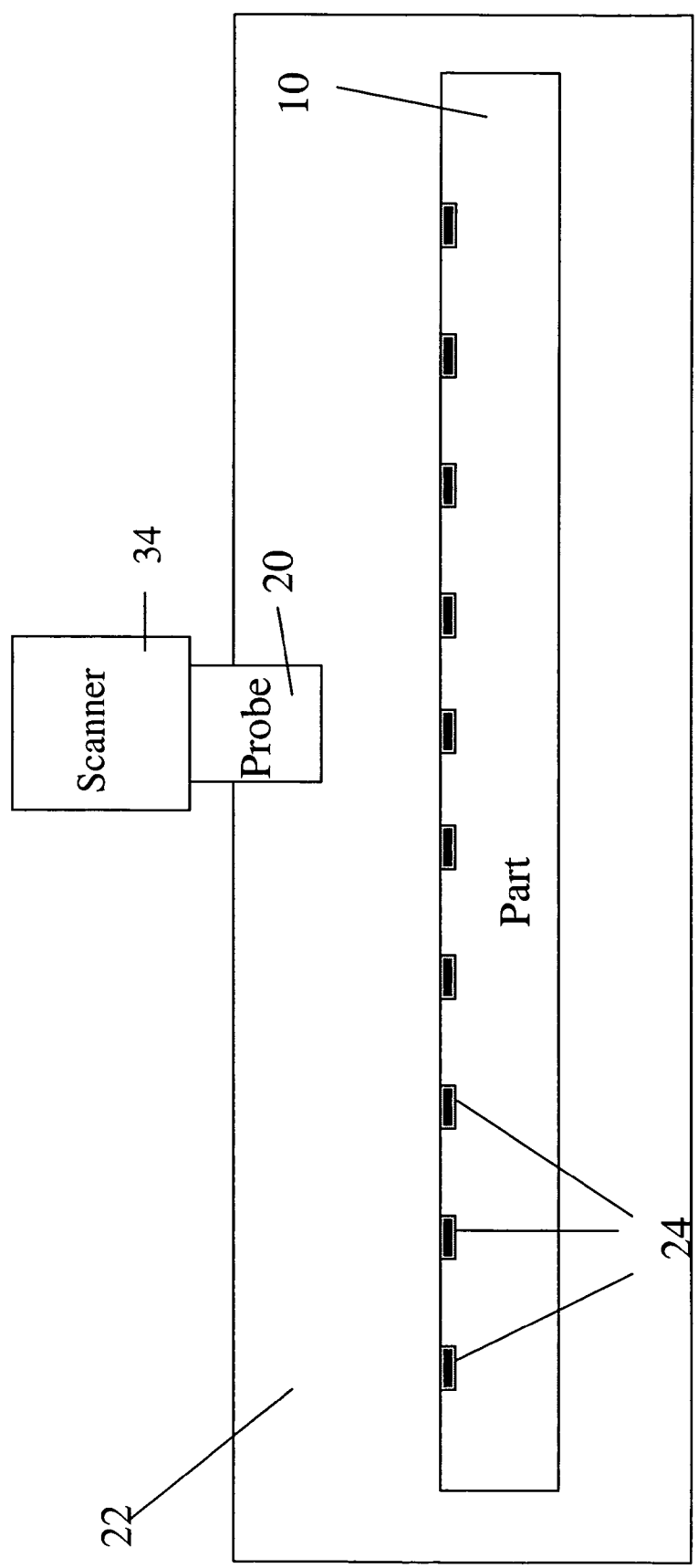
FIG. 6 shows a number of exemplary measurement positions.

For the exemplary embodiment of FIG. 3, a pulser/receiver circuit (or transmitter) 32 is configured to supply a number of signal excitation pulses to the transducer element 12 at a pulse repetition frequency (prf) of at least about 1000 Hz. A scanner 34 is configured to scan the component 10 with the ultrasonic probe 20 at a scanning rate equal to the prf times a scanning increment. A sample scanning increment is 0.02 inches. For example, the ultrasonic probe 20 may be mounted on a carriage of an electromechanical scanner 34 for moving the ultrasonic probe 20 to a number of positions relative to the component 10, as indicated in FIG. 6. Alternatively, the scanner 34 may be configured to move the component 10 relative to a fixed ultrasonic probe 20. Depending on the part geometry and desired inspection, a rectilinear, cylindrical or a circular scan may be employed. Additionally, the echo signals generated by the transducer 12 may be received by pulser/receiver circuit (or receiver) 32 for additional processing, storage and/or display by processing, storage and display modules, shown as a computer 38, acquisition software 40, and display 41 in FIG. 3. For the example embodiment of FIG. 3, the computer 38 is connected to the pulser/receiver 32 through an analog-to-digital (A/D) converter 42.

Another ultrasonic inspection system 50 embodiment of the invention is described with reference to FIGS. 7 and 8. For this embodiment, the ultrasonic probe comprises a number of transducer elements 12 forming an array 26, as shown for example in FIG. 7. The convex lens 14 extends over each of the transducer elements, and pulser/receiver 32 is configured to apply a separate excitation signal pulse to each of the transducers elements. The pulser/receiver 32 may be coupled to the transducer elements 12 via multiplexer 46, as show for example in FIG. 8. For example, for N transducer elements and M phase channels, an N×M multiplexer 46 may be used to couple the N transducer elements to M pulser/receiver circuits 32. For this example, M A/D converters 42 are used to connect a Delay and Sum Beam-former 44 to the M pulser/receiver circuits 32. The Beam-former 44 is connected to the computer 38.

According to a more particular embodiment, the acoustic impedance of the convex lens 14 is less than about $2.0 \times 10^6$ Rayls. Still more particularly, the acoustic impedance of the convex lens 14 is less than about $1.5 \times 10^6$ Rayls. As noted above, conventional ultrasonic testing techniques typically require long inspection times due to the unattenuated sound that reverberates in the coupling medium 22 that is being used to couple ultrasonic energy to the component 10. Beneficially, ultrasonic probe 20 reduces the unattenuated sound due to its improved impedance matching with the coupling medium 22.

Generally, the ability of convex lens 14 to absorb ultrasonic energy from the coupling medium 22 depends primarily on the impedance matching between the lens 14 and coupling medium 22. As used herein, "acoustic impedance" is the product of the ultrasonic velocity and the density. In particular, the reflection coefficient R at an interface between a first and a second material is governed by the following equation:

$$R=(Z_2-Z_1)/(Z_2+Z_1),$$

where $Z_1$ is the acoustic impedance of the first material, and $Z_2$ is the acoustic impedance of the second material.

As noted above, water is a typical coupling medium 22. The acoustic impedance of water at room temperature is approximately $1.5 \times 10^6$ Rayls. A typical acoustic impedance value for a conventional industrial lens material is in a range of about $3.0 \times 10^6$ Rayls to about $4.5 \times 10^6$ Rayls. For an exemplary conventional lens material with acoustic impedance of about $4.5 \times 10^6$ Rayls, the reflection coefficient is R=0.5 (or 50%). This means that, for a conventional industrial lens, fifty percent (50%) of the sound pressure is reflected off the surface of the lens.

Figure 5:
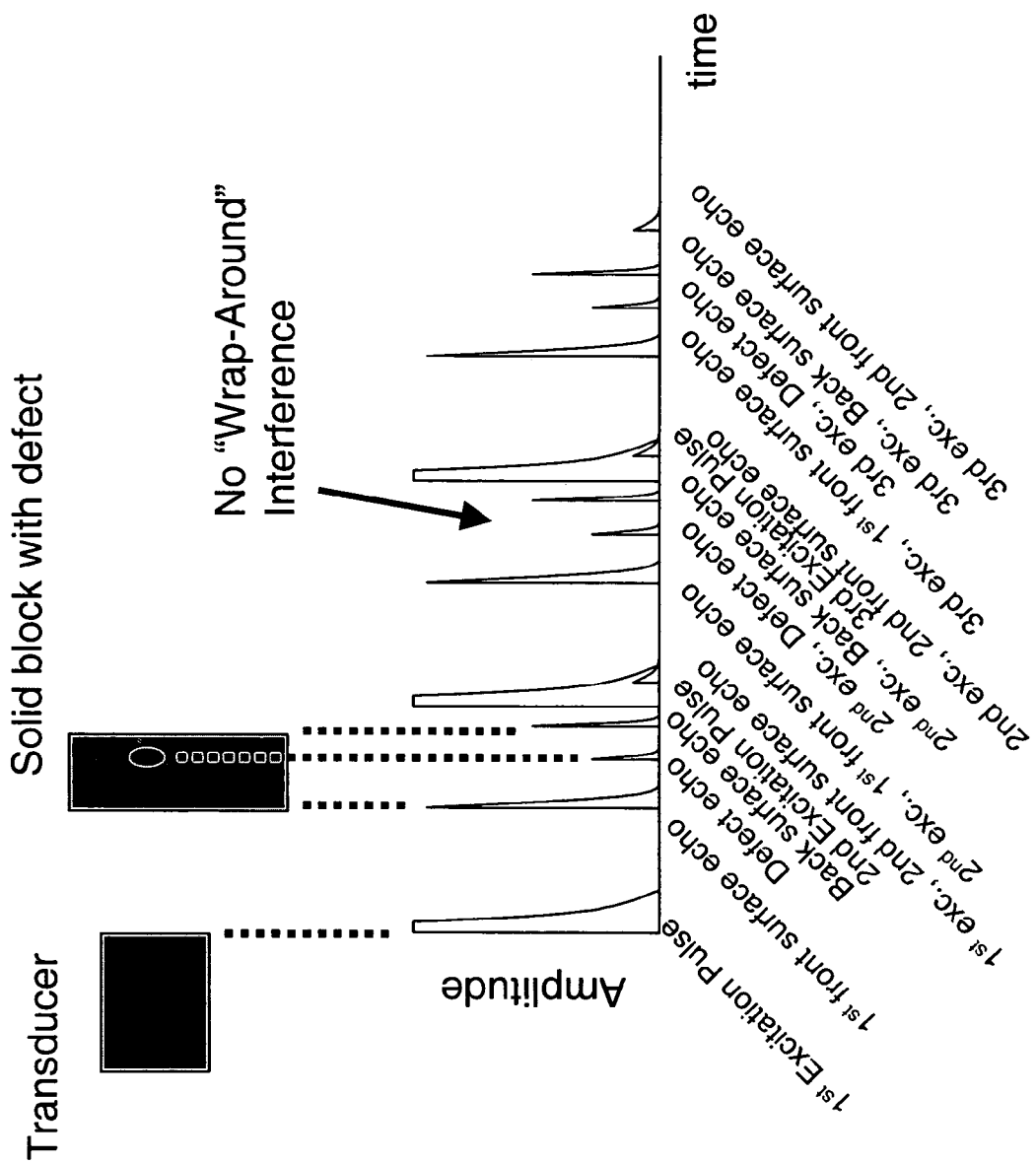
FIG. 5 is an exemplary A-scan display for an ultrasonic immersion test using the inspection system of FIG. 3 and shows the increased attenuation of waterpath multiples, with a corresponding increase in testing speed.

In contrast, an exemplary material for the convex lens 14 is a room temperature vulcanizing (RTV) material, examples of which include silicones. An exemplary RTV material for the convex lens 14 has an acoustic impedance of about $1.38 \times 10^6$ Rayls, which corresponds to a reflection coefficient of R=0.042 (or 4.2%) when water is employed as the coupling medium 22. The increased absorption of ultrasonic energy by convex lens 14 at the lens-coupling medium interface 18 results in the presence of correspondingly less ultrasonic energy in the coupling medium 22. This reduction in unattenuated sound facilitates the use of a higher prf, for example 1000 Hz, without comprising flaw detection. FIG. 5 shows increased attenuation of waterpath multiples, with a corresponding increase in testing speed.

Figure 4:
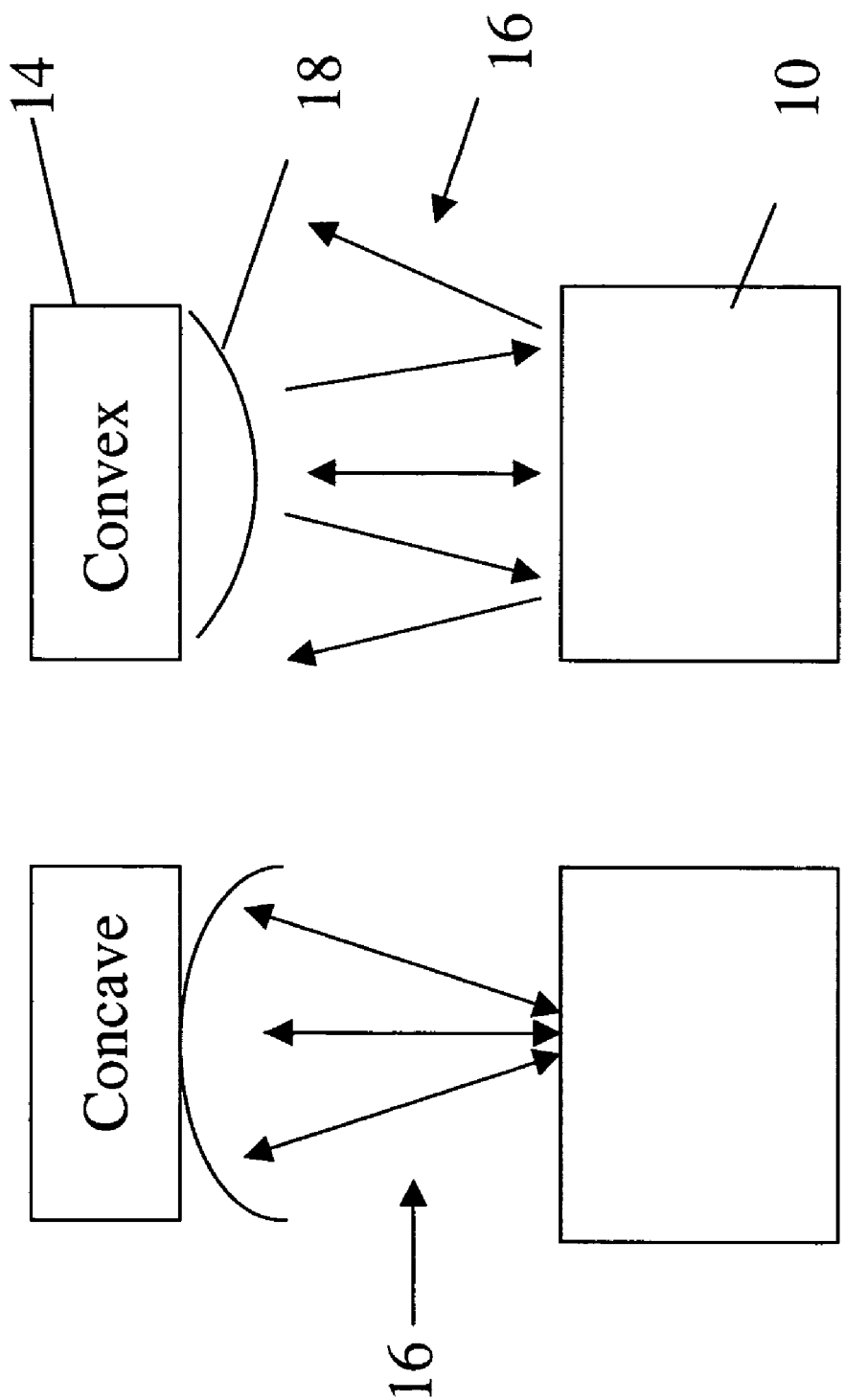
FIG. 4 shows the scattering properties of a convex lens as compared to a conventional concave lens.

A scattering feature of convex lens 14 is described with reference to FIG. 4, which illustrates the difference between a conventional concave industrial lens and the convex lens 14. As indicated in FIG. 4, the conventional concave lens focuses the incident acoustic waves 16 back into the coupling medium 22, which results in a number of multiple reflections at the surface 18 of the lens (or water-path multiples"). In contrast, convex lens 14 is desirably configured to scatter a number of acoustic waves 16 reflected from a surface 18 of the convex lens 14. By scattering the waves 16 away from ultrasonic probe 20, concave lens 14 further reduces the number of water-path multiples detected by ultrasonic probe 20, permitting a corresponding increase in testing speed.

The ability of a lens to scatter ultrasonic energy depends primarily on its geometry. As the primary function of the lens 14 is to focus the ultrasonic energy, and as the focal properties are predetermined for the given test, the lens geometry cannot be arbitrarily changed to enhance scattering at the lens-coupling medium interface 18. However, the acoustic velocity $c_L$ of the lens 14 provides an additional means to achieve the desired focal and scattering properties simultaneously. In particular, the lens geometry used to obtain a specific focal characteristic depends on the acoustic velocity $c_L$ of the lens material and is governed by the lens-maker's equation:

$$R=f(1-c_w/c_L),$$

where r is the radius of curvature of the lens, and f is the desired focal length. As noted above, $c_w$ is the acoustic velocity for the coupling medium 22, and $c_L$ is the acoustic velocity for the lens material. For a conventional lens for industrial immersion inspection, a typical lens material acoustic velocity $c_L$ is three kilometers per second (3.0 km/s). If water is used as the coupling medium 22 ($c_w$=1.5 km/s), the lens equation reduces to r=0.5 f, for this exemplary conventional lens. Because the relationship between the radius of curvature r and the focal length f is positive, this exemplary conventional lens is concave.

Conversely, convex lens 14 desirably has an acoustic velocity $c_L$ that is less than the material velocity $c_w$ of the coupling medium 22. For example an exemplary RTV material has an acoustic velocity $c_L$ of about one kilometer per second (1.0 km/s). For this exemplary RTV material, the lens equation becomes r=−0.5 f, and the negative sign indicates that the lens is convex. As indicated in FIG. 4, this change from a conventional concave to a convex geometry is significant, in that the concave geometry tends to focus ultrasonic energy in the coupling medium 22, particularly when the distance between the transducer and the component is equal to the lens radius. In contrast, the convex geometry of convex lens 14 scatters sound to the sides of the transducer, which reduces the amplitude of sound reverberations in the coupling medium 22. As discussed above with reference to FIG. 5, by increasing the attenuation of the waterpath multiples, the testing speed may be increased without compromising flaw detection. Accordingly, for more particular embodiments, the pulser/receiver 32 is configured to supply the signal excitation pulses to the transducer element 12 at a prf of at least about 1500, 5000, or 10,000 Hz. Beneficially, the increased prf results in a shorter inspection time, increasing inspection throughput.

The focal geometry for industrial ultrasound inspections typically differs from that for medical applications. In particular, the focal characteristics for industrial tests are selected for targeting solid (or non-liquid) objects and to accommodate two-layer issues (for example, metal/water interface issues) not present in medical ultrasound applications. Although the specific focal characteristics desired can vary based on the test to be performed, medical applications typically require a F# of about one and a half (f=1.5). As used herein, the F# is equal to the focal length divided by the aperture width of the transducer. In contrast, for a particular embodiment of the inspection system 30, the convex lens 14 has a F# of at least about four (4). According to a more particular embodiment, the convex lens 14 has a F# of at least about eight (8).

The probe may include a single transducer element, a linear array of transducer elements (not shown), or a two dimensional array of transducer elements, as shown for example in FIG. 7. Pulser/receiver 32 is configured to apply a separate excitation signal pulse to each of the transducers elements 12. For the exemplary embodiment of FIG. 7, ultrasonic probe 20 includes a number of transducer elements 12 forming an array 26 and one convex lens 14 that extends over each of the transducer elements 12. Pulser/receiver 32 is configured to apply a separate excitation signal pulse to each of the transducers elements 12. According to a particular embodiment, the array 26 is a phased array 26.

An exemplary ultrasonic probe 20 embodiment of the invention for immersion inspection of industrial components 10 in a coupling medium 22 with material velocity $c_w$ is described with reference to FIG. 3. As indicated in FIG. 3, the ultrasonic probe 20 includes at least one transducer element 12 configured to produce an ultrasonic pulse directed into the industrial component 10 through the coupling medium 22 upon excitation and to generate a number of echo signals. Ultrasonic probe 20 further includes at least one convex lens 14 with an acoustic impedance of less than about $2.5 \times 10^6$ Rayls and a F# of at least about four (4). Convex lens 14 is ultrasonically coupled to each of the transducer elements 12.

According to a particular embodiment, the F# of the convex lens 14 is at least about eight (8). According to more particular embodiments, the acoustic impedance of the convex lens 14 is less than about $2.0 \times 10^6$ Rayls, and more particularly less than about $1.5 \times 10^6$ Rayls. Desirably, the acoustic velocity $c_L$ of the convex lens 14 is less than the material velocity $c_w$ of the coupling medium 22, such that the convex lens 14 scatters the acoustic waves 16 reflected from the surface 18 of the convex lens 14, as indicated in FIG. 4, for example.

As discussed above with reference to FIG. 7, the ultrasonic probe 20 can include a single transducer element, a linear array of transducer elements (not shown), or a two dimensional array of transducer elements, as shown for example in FIG. 7.

A method embodiment of the invention is described with reference to FIGS. 3–6. As indicated, for example, in FIGS. 3 and 6, the inspection method includes immersing the component 10 in a coupling medium 22 with a material velocity $c_w$ and immersing ultrasonic probe 20 in the coupling medium. As noted above, ultrasonic probe 20 includes transducer 12 and convex lens 14 with an acoustic impedance of less than about $2.5 \times 10^6$ Rayls. To further enhance coupling, the acoustic impedance of the lens 14 is less than about $2.0 \times 10^6$ Rayls and still more particularly, less than about $1.5 \times 10^6$ Rayls, for particular embodiments. The inspection method further includes exciting transducer 12 to produce an ultrasonic pulse directed into the component 10 and generating a number of echo signals using transducer 12 as a receive element 12. According to a particular embodiment, transducer 12 is excited by applying an excitation signal pulse to the transducer at a prf of at least about 1000 Hz and more particularly, at prfs of at least about 1500, 5000, and 10,000 Hz, depending on the desired inspection throughput rate. Beneficially, because of the improved coupling of lens 14 to the coupling medium 22, these higher prfs can be achieved without comprising flaw detection, as shown for example in FIG. 5.

As indicated, for example, in FIG. 6, the inspection method further includes scanning the component 10 with the ultrasonic probe 20 at a scanning rate equal to the prf times a scanning increment and performing the exciting and generating steps at each of a number of measurement positions 24. As noted above, one typical scanning increment is about is 0.02 inches. For the sample embodiment of FIG. 3, the scanning is performed using scanner 34, which may be controlled by computer 38. Although FIG. 3 shows a scanner 34 configured to move the probe 20 relative to the component 10, a scanner may also be configured to move the component relative to a fixed probe, and the inspection method encompasses both configurations.

As shown, for example, in FIG. 4, the inspection method further includes scattering a number of acoustic waves 16 reflected from the surface 18 of the convex lens 14. To scatter the acoustic waves, reflected from the surface 18, the material for the convex lens 14 is selected such that its acoustic velocity $c_L$ is less than the material velocity $c_w$ of the coupling medium 22, as discussed above.

According to a particular embodiment, the ultrasonic probe 20 includes a number of transducers 12 forming an array 26, as shown for example in FIG. 7. The array may also be a linear array. For this exemplary embodiment, each of the transducers is excited, and a number of echo signals are generated using the transducers 12 as receive elements. According to a more particular embodiment, a separate excitation signal pulse is applied to each of the transducers 12 at a prf of at least about 1000 Hz and, more particularly, at prfs of at least about 1500, 5000, and 10,000 Hz. Generally, the same prf ranges are employed for single transducer and array embodiments.

An exemplary ultrasonic inspection method for testing industrial components 10 includes exciting at least one transducer element 12 of an ultrasonic probe 20 to produce an ultrasonic pulse directed into the industrial component.

The ultrasonic probe and the industrial component are separated by a standoff filled with a coupling medium 22 with a material velocity $c_w$, as indicated in FIG. 3, for example. The ultrasonic inspection method further includes enhancing a coupling of the at least one transducer element 12 to the coupling medium 22 using a lens 14 having an acoustic impedance of less than about $2.5 \times 10^6$ Rayls, and more particularly, less than about $2.0 \times 10^6$ Rayls. The ultrasonic inspection method further includes scattering a number of acoustic waves 16 reflected from a surface 18 of the lens by using a convex lens 14, and generating a number of echo signals using at least one transducer 12 as a receive element 12. According to a particular embodiment, at least one transducer 12 is excited by applying an excitation signal pulse to at least one transducer 12 at a prf of at least about 1500 Hz. For the exemplary embodiment of FIG. 3, the ultrasonic inspection method further includes immersing the ultrasonic probe 20 and the industrial component 10 in the coupling medium 22.

For the exemplary embodiment of FIG. 6, the ultrasonic inspection method further includes scanning the industrial component 10 with the ultrasonic probe 20 at a scanning rate equal to the prf times a scanning increment. The exciting, enhancing, scattering and generating steps are performed at each of a number of measurement positions 24 for the ultrasonic probe.

As discussed above with reference to FIG. 7, the probe 20 may include a single transducer element 12, a linear array of transducers, or a two dimensional array of transducer elements, as shown for example in FIG. 7. According to a particular embodiment, the ultrasonic probe 20 includes a number of transducers 12 forming an array 26. For this exemplary embodiment, each of the transducers 12 is excited, and a number of echo signals are generated using the transducers as receive elements. For a more particular embodiment, a separate excitation signal pulse is applied to each of the transducers 12.

Although only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of inspecting a component comprising:
   immersing the component in a coupling medium with a material velocity $c_w$;
   immersing an ultrasonic probe comprising at least one transducer in the coupling medium, the ultrasonic probe further comprising a convex lens with an acoustic velocity $c_L$ and an acoustic impedance of less than about $2.5 \times 10^6$ Rayls;
   exciting the at least one transducer to produce an ultrasonic pulse directed into the component, wherein said exciting the at least one transducer comprises applying an excitation signal pulse to the at least one transducer at a pulse repetition frequency (prf) of at least about 1000 Hz;
   generating a plurality of echo signals using the at least one transducer as a receive element; and
   scanning the component with the ultrasonic probe at a scanning rate equal to the pulse repetition frequency times a scanning increment, wherein said exciting and generating steps are performed at each of a plurality of measurement positions for the ultrasonic probe.

2. The inspection method of claim 1, wherein the pulse repetition frequency (prf) is at least about 5000 Hz.

3. The inspection method of claim 1, further comprising: scattering a plurality of acoustic waves reflected from a surface of the convex lens, wherein the acoustic velocity $c_L$ of the convex lens is less than the material velocity $c_w$ of the coupling medium.

4. The inspection method of claim 1, wherein the ultrasonic probe comprises a plurality of transducers forming an array, wherein said exciting comprises exciting each of the transducers, wherein said generating comprises generating a plurality of echo signals using the transducers as receive elements, and wherein said exciting comprises applying a separate excitation signal pulse to each of the transducers.

5. An ultrasonic inspection method for testing industrial components, said method comprising:
   exciting at least one transducer element of an ultrasonic probe to produce an ultrasonic pulse directed into the industrial component, wherein the ultrasonic probe and the industrial component are separated by a standoff filled with a coupling medium with a material velocity $c_w$, wherein said exciting at least one transducer comprises applying an excitation signal pulse to the at least one transducer at a pulse repetition frequency (prf) of at least about 1500 Hz;
   enhancing a coupling of the at least one transducer element to the coupling medium using a lens having an acoustic impedance of less than about $2.5 \times 10^6$ Rayls;
   scattering a plurality of acoustic waves reflected from a surface of the lens, wherein said scattering comprises using a convex lens;
   generating a plurality of echo signals using the at least one transducer as a receive element; and
   scanning the industrial component with the ultrasonic probe at a scanning rate equal to the pulse repetition frequency (prf) times a scanning increment, wherein said exciting, enhancing, scattering and generating steps are performed at each of a plurality of measurement positions for the ultrasonic probe.

6. The ultrasonic inspection method of claim 5, further comprising:
   immersing the ultrasonic probe and the industrial component in the coupling medium.

7. The ultrasonic inspection method of claim 5, wherein the ultrasonic probe comprises a plurality of transducers forming an array, wherein said exciting comprises exciting each of the transducers, wherein said generating comprises generating a plurality of echo signals using the transducers as receive elements, and wherein said exciting comprises applying a separate excitation signal pulse to each of the transducers.

8. An ultrasonic inspection system for testing a component using a coupling medium, said ultrasonic inspection system comprising:
   an ultrasonic probe comprising:
      (a) at least one transducer element configured to produce an ultrasonic pulse directed into the component through the coupling medium upon excitation and to generate a plurality of echo signals;
      (b) a convex lens having an acoustic impedance of less than about $2.5 \times 10^6$ Rayls, wherein said convex lens is ultrasonically coupled to each of said transducer elements;
   a pulser/receiver configured to supply a plurality of signal excitation pulses to said at least one transducer element at a pulse repetition frequency (prf) of at least about 1000 Hz; and a scanner configured to scan the component with the ultrasonic probe at a scanning rate equal to the pulse repetition frequency (prf) times a scanning increment.

9. The ultrasonic inspection system of claim 8, wherein the acoustic impedance of said convex lens is less than about $2.0 \times 10^6$ Rayls, and wherein said convex lens is configured to scatter a plurality of acoustic waves reflected from a surface of said convex lens.

10. The ultrasonic inspection system of claim 9, wherein said convex lens has an acoustic velocity $c_L$ that is less than a material velocity $c_w$ of the coupling medium, and wherein said pulser/receiver is configured to supply the signal excitation pulses to said at least one transducer element at the pulse repetition frequency (prf) of at least about 1500 Hz.

11. The ultrasonic inspection system of claim 10, wherein said at least one convex lens has a F# of at least about eight (8).

12. The ultrasonic inspection system of claim 8, wherein said ultrasonic probe comprises a plurality of transducer elements forming an array, wherein said convex lens extends over each of said transducer elements, and wherein said pulser/receiver is configured to apply a separate excitation signal pulse to each of said transducers elements.

13. The ultrasonic inspection system of claim 12, wherein said array is a phased array.

* * * * *